(12) United States Patent
Jackson

(10) Patent No.: US 6,699,248 B2
(45) Date of Patent: Mar. 2, 2004

(54) MULTIPLE DIAMETER TANGENTIAL SET SCREW

(76) Inventor: Roger P. Jackson, 4706 W. 86th St., Prairie Village, KS (US) 66207

(*) Notice: Subject to any disclaimer, the term of this patent is extended or adjusted under 35 U.S.C. 154(b) by 0 days.

(21) Appl. No.: 10/143,120

(22) Filed: May 9, 2002

(65) Prior Publication Data

US 2003/0212398 A1 Nov. 13, 2003

(51) Int. Cl.$^7$ .............................................. A61B 17/56
(52) U.S. Cl. ................................. 606/61; 606/73; 411/3
(58) Field of Search ............................... 606/61, 53, 54, 606/57, 64, 66, 72, 73; 403/362, 382, 394; 411/393, 3, 2, 4, 5, 405, 402, 403

(56) References Cited

U.S. PATENT DOCUMENTS

| | | |
|---|---|---|
| 4,763,644 A | 8/1988 | Webb |
| 5,005,562 A | 4/1991 | Cotrel |
| 5,127,912 A | 7/1992 | Ray et al. |
| 5,147,360 A | 9/1992 | Dubousset |
| 5,382,248 A | 1/1995 | Jacobson et al. |
| 5,476,463 A | 12/1995 | Boachie-Adjei et al. |
| 5,499,892 A * | 3/1996 | Reed ............................. 411/5 |
| 5,514,132 A * | 5/1996 | Cserntony et al. ............ 606/61 |
| 5,522,816 A * | 6/1996 | Dinello et al. ................ 606/61 |
| 5,584,831 A * | 12/1996 | McKay ......................... 606/61 |
| 5,643,260 A | 7/1997 | Doherty |
| 5,676,665 A * | 10/1997 | Bryan ........................... 606/61 |
| 5,697,929 A | 12/1997 | Mellinger |
| 5,716,355 A | 2/1998 | Jackson et al. |
| 5,779,704 A * | 7/1998 | Kim .............................. 606/64 |
| 5,800,434 A * | 9/1998 | Campbell, Jr. ................ 606/61 |
| 5,928,236 A * | 7/1999 | Augagneur et al. ........... 606/73 |
| 5,947,966 A | 9/1999 | Drewry et al. |
| 5,980,523 A | 11/1999 | Jackson |
| 6,039,738 A * | 3/2000 | Sanders et al. ............... 606/61 |
| 6,059,786 A | 5/2000 | Jackson |
| 6,074,391 A * | 6/2000 | Metz-Stavenhagen et al. ............................. 606/61 |
| 6,074,393 A * | 6/2000 | Sitoto ........................... 606/73 |
| 6,077,267 A * | 6/2000 | Huene .......................... 606/73 |
| 6,102,913 A | 8/2000 | Jackson |
| 6,136,003 A | 10/2000 | Hoeck et al. |
| 6,238,396 B1 * | 5/2001 | Lombardo .................... 606/61 |
| 6,261,288 B1 | 7/2001 | Jackson |
| 6,283,967 B1 * | 9/2001 | Troxell et al. ................ 606/61 |
| 6,368,321 B1 * | 4/2002 | Jackson ........................ 606/61 |
| 6,402,749 B1 * | 6/2002 | Ashman ....................... 606/61 |
| 6,432,108 B1 * | 8/2002 | Burgess et al. ............... 606/61 |
| 6,475,218 B2 * | 11/2002 | Gournay et al. ............. 606/61 |

* cited by examiner

Primary Examiner—Eduardo C. Robert
Assistant Examiner—David C. Comstock
(74) Attorney, Agent, or Firm—John C. McMahon

(57) ABSTRACT

A multiple diameter tangential set screw particularly for securing a rod within a hook shaped rod receiver includes a threaded mounting segment, a threaded rod engaging segment, and an abutment surface at a transition between the mounting segment and the rod engaging segment. The mounting segment has a larger diameter than the rod engaging segment and is received in a threaded bore formed in the rod receiver. The abutment surface has a concavely radiused surface of revolution. The rod engaging segment is positioned so that threads of the rod engaging segment cut into the surface of the rod to secure the rod from rotational movement. Engagement of the rod engaging segment and the abutment surface cooperate to urge the rod into frictional engagement with the rod receiver and to secure it from axial, radial and rotational displacement relative to the rod receiver.

31 Claims, 1 Drawing Sheet

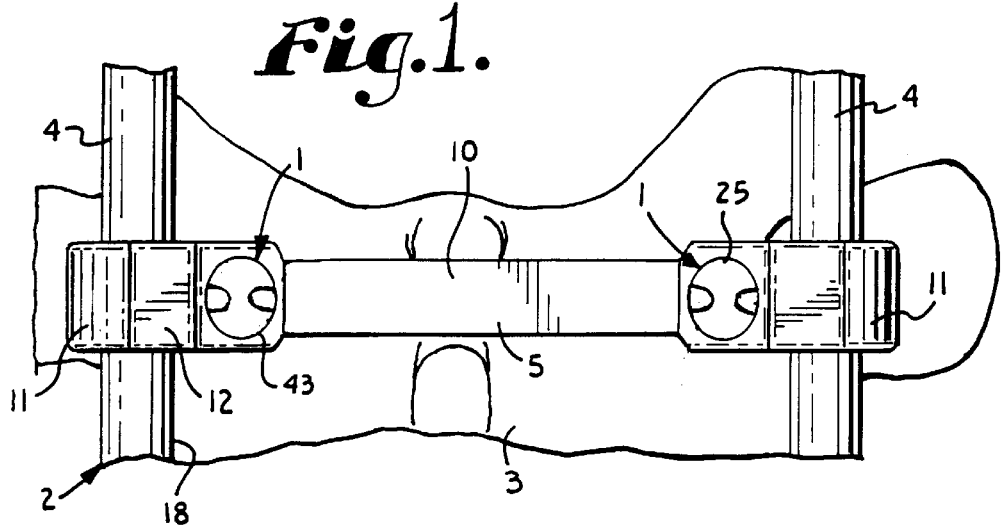
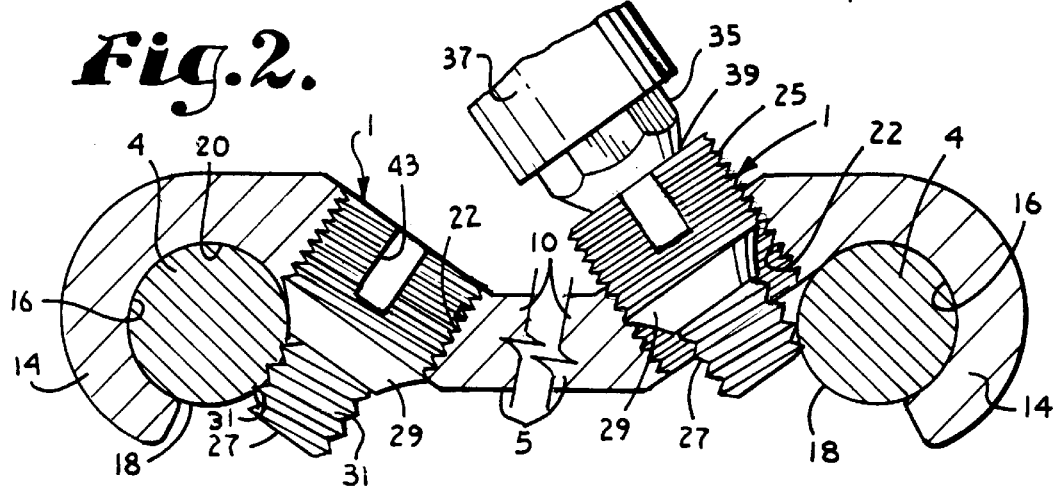
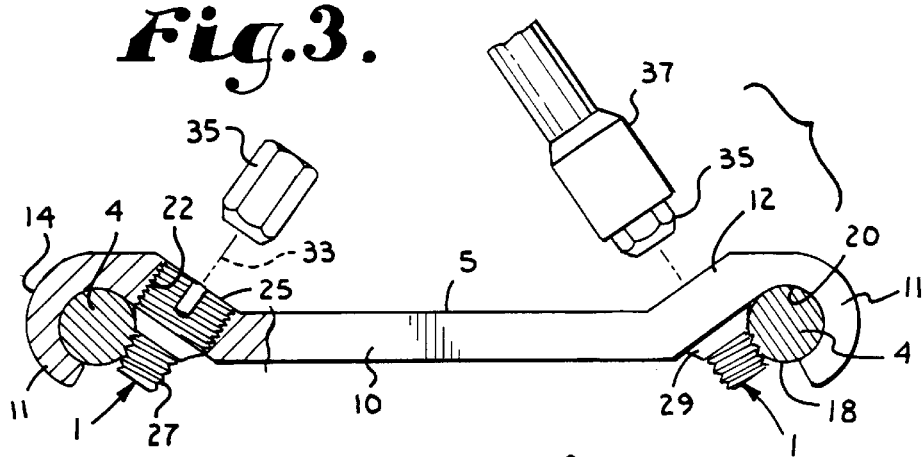

MULTIPLE DIAMETER TANGENTIAL SET SCREW

BACKGROUND OF THE INVENTION

The present invention is directed to a set screw for tangentially engaging a spine fixation rod and, more particularly, to such a set screw having a pair of coaxial or co-linear screw shafts with different diameters and separated by an abutment or bearing surface to urge the rod into frictional engagement with the inner surface of a receiving member and to positively engage the surface of the rod to prevent axial and non-axial displacement of the rod and rotation of the rod relative to the receiving member.

The art of correcting back deformities, injuries and the like has advanced dramatically in recent years. Surgeons who perform operations on the spine and related bones of the body are constantly developing new procedures and techniques that require implants which are capable of being stable in the body after implantation and which firmly lock in place to resist the substantial pressures and forces developed by the body on the implant. Such implants must often also resist twisting or torsion applied to parts of the implant, and certain prior art implants have not always been successful at resisting twisting or torsion.

Such implants often involve rods which are placed along the spinal column or various bones of the living body and preshaped or, once secured to the bones, such rods may be bent and/or further shaped to force the bones to align with the rods and, in this manner, provide correction to misalignment of the bones or bone parts caused by deformity, injury or the like. That is, one or more rods are placed in the correct curvature for the spine and the spinal bones are joined to the rod or rods, before or after bending the rods, in such a manner as to thereafter force the bones to follow the same configuration as the rods.

Once the rods are bent, forces created by the muscles of the patient, by sudden movement, by accident, or the like often act to try to rotate or apply torque to the implant as a whole or to a rod individually. Such forces generally apply torsion to the apparatus which may act to loosen or even dislodge the implant or to turn or rotate one or more rods to a less effective support position. It is desirable that the apparatus be able to resist such forces acting upon it.

Historically, the rods used as implants in the manner described above, are typically joined with various bones along the length of the rod by use of bone screws or other implants that are joined with the rod. It has been found that conventionally available implants join rods to bone screws or intermediate connectors in such a manner that the rods are often held against axial movement relative to the bone screws or intermediate connector. That is, the rods are not likely to move substantially with respect to the other implants in a direction that is along the central or longitudinal axis of the rod. However, because of the substantial forces exerted on the rod during use, certain forces act to try to rotate the rod within bone screws and connectors, such that the spinal corrective configuration and positioning of the rod can slip due to rotation of the rod from an optimal position to one that is less suited for the patient. This can occur when substantial forces are applied to the back during exercise, accident or the like.

Consequently, it is desirable to have an implant that not only effectively resists axial movement of the rod relative to the other implants, but also effectively resists torque or torsion that produce turning of the rod or rotation of the rod relative to the implants. One use of the present invention is especially suited for the locking and stabilizing a posterior spinal implant system having at least one, but normally a pair of elongate rods that extend along the spine. In particular, the installation of spinal rods is often utilized to reposition the spine and correct deformities and the like. Such a rod is typically anchored at opposite ends to vertebrae and is likewise joined with vertebrae along the length of the rod by bone screws or the like. The system is typically installed by curving the rod to fit the malformed spine of the patient and then securing the anchors at both ends and various intermediate bone screws to the rod. The rod is thereafter bent by rod bending tools to assume the desired configuration of the spine and the rod in this manner translates the various bones of the spine along with it to the correct configuration.

Once the rod is bent, the body exerts forces, including substantial rotational forces or torsion on the rod, especially should the patient be struck on the back, during exercising, or the like. It is also noted that the rod can first be bent and then the bone moved to the rod and secured to the rod. In either case, it is important that the anchors at opposite ends of the rod and at the bone screws along the rod resist rotation of the rod and that the anchors themselves remain stable and securely attached to an associated bone. Furthermore, it is important to both lock the rod against rotation in or relative to the bone screw and to secure the anchors of the rod against rotation relative to the spine.

An implant system is therefore desirable that provides a strong anchor at opposite ends of the rod and at bone screws along the rod that resists rotation of the rod both relative to the bone screws and relative to the spine during procedures at the time of implantation and later during use and that such a system also resist axial displacement of the rod relative to anchoring bone screws and other bracing members used in the system.

SUMMARY OF THE INVENTION

The present invention provides a multiple diameter tangential set screw with an intervening concave, radiused abutment surface for securing a rod against axial and rotational movement relative to a member in which the rod is received. The present invention has particularly advantageous application in implanted bone and spinal fixation components. The rod receiving member may be an open hook type connector of a rod anchor, a cross connector, or other type of element to which a rod is to be secured in the manner wherein a rod is biased into a hook like receiver and then held therein against radial, axial or rotational relative movement. Alternatively, the rod receiver can be a closed type of element. The rod receiver has a rod receiving opening with a surface that is in at least partially surrounding relation to the rod when the rod is in the receiver. A threaded set screw bore is formed in partially intersecting relation to the rod receiving opening.

The set screw has a threaded mounting segment which has a diameter and threading compatible with the set screw bore. A threaded rod engaging segment extends coaxially from the mounting segment and has a reduced diameter relative to the mounting segment. An abutment or bearing surface provides a transition between the mounting segment and the rod engaging segment. In a preferred embodiment of the present invention, the abutment surface is a concavely radiused surface of revolution with a radius substantially equal to the radius of the rod with which the set screw will be used.

The position and relative angle of the set screw bore and the radius of the rod engaging segment are configured in such a manner that the abutment surface forces the rod into frictional engagement with the surrounding surface of the rod opening to thereby clamp the rod between the rod receiver and the abutment surface of the set screw. Such clamping resists relative radial movement and axial movement of the rod along its longitudinal axis and, to some extent, resists rotational movement of the rod within the rod receiver. The threads of the rod engaging segment of the set screw cut into the surface of the rod to positively resist and secure the rod against rotational movement.

In an implant implementation of the present invention, the set screw is formed with a break off driving or installation head, such as of a hexagonal configuration, which is connected to the mounting segment of the set screw by a weakened cross section or torque limiting region. The weakened area causes the installation head to break off the mounting segment at a preselected torque. The hex head facilitates use of a compatible installation tool to rotate and thereby advance the set screw into clamping engagement with the rod. The mounting segment of the set screw may also be provided with formations for engagement by a removal tool, such as a hexagonal socket and/or a set of peripheral slots that are parallel to the axis of rotation or the like.

OBJECTS AND ADVANTAGES OF THE INVENTION

Therefore, the objects of the present invention include: providing improved components for implanted bone fixation systems and, particularly, spinal fixation systems; providing improved fasteners for securing fixation rods to various other fixation components; providing, particularly, an improved set screw configuration for securing a connection joint between a rod and a rod receiving member; providing such a set screw which engages the rod and the rod receiving member frictionally and in such an interfering manner as to positively secure the rod within the receiving member; providing such a set screw which secures the rod against both axial and rotational movement relative to the rod receiver; providing, particularly, a multiple diameter set screw which is positioned at a partially intersecting or substantially tangential relation to the rod; providing such a set screw including a threaded mounting segment sized and threaded to fit within a threaded bore formed in the rod receiver member; providing such a set screw including a threaded rod engaging segment extending coaxially from the mounting segment and having such a diameter sized and shaped to interferingly or threadedly engage the surface of the rod, that is, to cut into the surface of the rod to positively fix the position of the rod within the rod receiver; providing such a set screw including an abutment or bearing surface which transitions between the mounting segment and the rod engaging segment and that is configured to engage the rod and urge it into frictional engagement with the surrounding surface of the rod receiving member; providing such a set screw in which the abutment surface is a concave radiused surface of revolution having a curvature or concave radius substantially equal to that of the rod to be secured within the rod receiver; providing such a set screw including a weakened section to form a break-off installation head which is adapted to separate at a preselected torque applied by an installation tool to the screw head; providing such a set screw including removal structure or formations to enable positive engagement by a removal tool for removal of the set screw from the rod receiver; providing such a set screw configuration which has advantageous application in implanted spinal fixation systems; providing such a set screw which is adaptable to applications other than such implanted systems; and providing such a multiple diameter tangential set screw which is economical to manufacture, which is effective in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary side elevational view of a spinal implant system including spaced apart rods interconnected by a cross member and secured in place by multiple diameter tangential set screws in accordance with the present invention.

FIG. 2 is an enlarged bottom plan view of the cross member in cross section and showing one of the set screws previously installed and also showing a second set screw being threaded into engagement with a rod by an installation tool.

FIG. 3 is a bottom plan view and illustrates the separation of breakaway heads of the set screws after installation in the implant system.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a multiple diameter tangential set screw which embodies the present invention. Although not restricted to such use, the set screw 1 is particularly advantageous within implanted spinal fixation systems 2 for correctively securing the relative positions and orientations of individual vertebrae 3 (FIG. 1) within the spine. Such fixation systems 2 often include elongated spinal fixation rods 4 interconnected by cross links or transverse members 5. The set screw 1 of the present invention is particularly adapted for securing joints between the cross members 5 and the rods 4.

The vertebrae 3 are components of the spine of a person or animal and are subject to misalignment and misorientation due to congenital deformity, degenerative age-related processes, injury, or the like. Spinal fixation systems 2 are used to correct the alignment and orientation of the individual vertebrae 3 to thereby correct the overall configuration of the spine.

In general, spinal fixation systems 2 include bone fasteners or screws (not shown) which are attached to or directly implanted in the vertebrae 3, and frame or structural members, such as the elongated rods 4 and cross members 5 which are connected to the bone fasteners. The rods 4 are sometimes preshaped, but more often are, after connection to the vertebrae, then shaped in such a manner as to urge the vertebrae 3 into the desired alignment and orientation. An example of such spinal fixation structure 2 is detailed in U.S. Pat. No. 6,261,288 which is incorporated herein by reference. The set screws 1 of the present invention are particularly well adapted for securing connections between the rods 4 and cross members 5 within spinal fixation systems 2, although other uses of the screws 1, in applications independent of medical implants, are contemplated.

The illustrated rods 4 are cylindrical in cross section and are preferably formed of a stainless steel or other body friendly metal or material. The rods 4 are generally very rigid and are not intended to be very flexible once installed. The rods are bent into desired shapes during placement using special tools. The cross members 5 connect between sets of the rods 4 at various locations spaced along the rods and form braces to stabilize the spinal fixation structure 2.

Each of the illustrated cross members, or rod receiving members, 5 includes an elongated central link or bar 10 with hooks 11 formed on the opposite ends of the central link 10. Each illustrated hook 11 includes a relatively straight section 12 and a bight or curved section 14. The curved section 14 has an inner surface 16 which is sized and shaped to closely contact and tightly abut against an outer surface 18 of a rod 4 in at least partially surrounding relation. The straight section 12, curved section 14, and inner surface 16 form a rod receiving opening 20 to receive and seat a rod 4. The illustrated opening is preferably an open ended hook 11 to facilitate connective engagement of the cross member 5 with the rod 4 without accessing an end of such a rod 4. That is, the rod 4 can simply be laid in the hook 11 without feeding the rod 4 by one end through the device. However, it should be noted that the set screw 1 could also be used with a structure having a closed ended rod receiver. The illustrated cross member 5 has a set screw receiving bore 22 formed in each straight section 12 thereof, the bore 22 being tapped with a thread that covers the entire surface thereof.

The set screw 1 has a mounting segment 25 and a rod engaging segment 27, with an abutment or bearing surface 29 providing a transition between the mounting segment 25 and the rod engaging segment 27. The mounting segment 25 has a diameter and thread compatible with that of the set screw bore 22. The rod engaging segment 27 preferably has an interference formation 31 on its outer surface, of such a configuration as to positively engage the outer surface 18 of the rod 4 to prevent it from rotating about its axis within the rod receiving opening 20. Preferably, the formation 31 cuts or bites into the rod 4. In the illustrated rod engaging segment 27, the interference formation 31 is a helical wound thread 31. The thread 31 is particularly beneficial in that it facilitates its own engagement with the surface 18 of the rod 4 by cutting a groove into the rod 4 that successive turns of the thread 31 follows, while effectively resisting rotation of the rod 4 within the opening 20 of the rod receiver 5. In particular, the leading edge of the thread 31 cuts a groove or track 30 on the rod 4 as it advances which is then followed by at least a portion of the remaining part of the thread 31 so as to preserve the tool 30 and so that the thread 31 remains at least partially seated inside the track 30.

The location of the bore 22 on the cross member 5, the angle of the bore 22 relative to the rod 4, and the diameter of the rod engaging segment 27 relative to the diameter of the rod 4 all result in the rod engaging segment 27 being positioned slightly radially inward of being tangential to the rod 4. The amount of difference between the actual placement and a true tangential placement defines the depth or extent the thread 31 cuts into the rod 4. The placement of the segment 27 relative to the surface 18 of the rod 4 enables the thread 31 to dig into the rod 4 through the surface 18 thereof during installation and to remain there after installation is complete to thereby positively resist rotation of the rod 4. Additionally, engagement of the segment 27 with the rod 4 urges a portion of the surface 18 of the rod 4 into frictional engagement with the inner surface 16 of the rod receiving opening 20 of the cross member 5. Such frictional engagement resists linear displacements of the rod 4 relative to the cross member 5, as well as angular or radial displacements.

In the illustrated set screw 1, the mounting segment 25 has a larger diameter than the diameter of the rod engaging segment 27. The structural transition between the larger diameter segment 25 and the smaller diameter segment 27 is provided by the abutment surface 29 which is employed in the set screw 1 of the present invention to provide additional rod securement or locking. The geometry of the rod receiver 5 is sized and shaped in such a manner that the surface 29 engages the outer surface 18 of the rod 4 when the set screw 1 is fully positioned in the bore 22, and the surface 29 urges the rod 4 into frictional engagement of a portion of the outer surface 18 with the inner surface 16 of the rod receiving opening 20 of the rod receiving member 5. The effects of the abutment surface 29 and the rod engaging segment 27 in urging portions of the rod surface 18 into contact with the inner surface 16 of the rod receiving opening 18 are complementary and increase the clamping forces applied by the cross member 5 onto the rods 4.

Although the abutment surface 29 could have any of a number of configurations, the preferred surface 29 has a concavely radiused surface of revolution about an axis 33 (FIG. 3) of the screw 1. That is, the surface 29 has a shape which is generated by revolving an arc, which is concave in a direction away from the axis 33, about the axis 33. Such an arc, and the concave radiusing, preferably has a radius substantially equal to the radius of the rod 4. By use of this geometry, the surface 29 closely engages the surface 18 of the rod 4 at least at one location or the surface 29 substantially along the entire top to bottom length of the arc. The illustrated surface 29 is smooth; however, it could alternatively have an interference formation, such as threading, circumferential grooves, knurling, or the like. Also, while the surface 29 is preferably concavely radiused, it could be of some other shape, such as frusto-conical.

It is generally preferred that the implanted structure and hardware be minimal in size and be as free as possible of edges and projections to avoid undesired interaction with organs and structure within the body. With regard to the present invention, it is desirable that the set screw 1 provide a strong and effective joint between a cross member 5 and a rod 4 while being minimal in size. To accomplish these objectives, the set screw 1 is formed with a break-off installation head 35 which extends axially from the mounting segment 25 of the screw 1. The head is configured in such a way as to enable positive engagement by a conventional socket type installation tool 37 for rotating the screw 1. The illustrated head 35 has a hexagonal shape for engagement by an appropriately configured tool 37. The head 35 joins the mounting segment 25 by way of a weakened region 39 which is reduced in cross sectional area in such a manner that the region 39 fails in response to a selected level of torque applied by the tool 37 to the head 35, thereby causing the head 35 to separate from the mounting segment 25. The torque at which the head 35 separates is of such a value as to result in a very secure joint between the cross member 5 and the rod 4. During installation of the spinal fixation system 2, once a head 35 separates from the mounting 25, it may be discarded since it has no further function.

In some applications of the present invention, the joints formed by the set screws 1 are permanent or virtually permanent. However, under some circumstances, it is desirable to remove a set screw 1 to release a joint between a cross member 5 and a rod 4. For these purposes, the set screw 1 is provided with formations for positive engagement of the screw 1 by a screw removal tool (not shown) of complementary configuration. The illustrated set screw 1 is provided with a pair of side slots or grooves 43, both formed into the mounting segment 25. Further description of such slots is provided in U.S. Pat. Nos. 6,059,786 and 6,102,913 which are incorporated herein by reference. Other removal structure such as a hex or torqux shaped residual bore becomes accessible after the head 35 breaks away can be used for this purpose.

It is foreseen that the present invention can be used in a wide variety of implants wherein either a rod needs to be anchored securely or wherein it is desirable to prevent both axial and rotational movement of the rod relative to the implant. The present invention can be used in conjunction with both open implants such as hooks or closed implants such as the enclosed heads shown in certain of the embodiments.

It is to be understood that while certain forms of the present invention have been illustrated and described herein, it is not to be limited to the specific forms or arrangement of parts described and shown.

What is claimed and desired to be secured by Letters Patent is:

1. A fastener sized and shaped so as to be adapted to secure an elongate rod within a rod receiving member wherein the rod has a rod axis and a rod surface and the receiving member has a threaded bore; said fastener comprising:
    (a) a first shaft segment having a fastener axis and a first radius with a threaded outer surface adapted to be threaded into said threaded bore about an axis of rotation;
    (b) a second shaft segment having a second radius of a smaller size than said first radius and extending coaxially from said first shaft segment;
    (c) said first shaft segment being rigid and shaped bore to be rotatably received within the so as to retain said first shaft segment therein with said second shaft segment extending outwardly from the bore; and
    (d) said fastener being sized and shaped so that when said shaft first segment is fully received in said bore, said second shaft segment second radius is sized such that said second shaft segment interferingly engages said rod surface along a substantial segment thereof to thereby inhibit rotation of said rod about said rod axis and translation of said rod along said rod axis relative to the receiving member.

2. The fastener as set forth in claim 1 and including:
    (a) an abutment surface connecting said first shaft segment and said second shaft segment and sized and positioned to at least partially engage the rod surface when said first shaft segment is fully in the bore to urge the rod into frictional engagement with the receiving member.

3. The fastener as set forth in claim 2 wherein:
    (a) said abutment surface is a concave surface of revolution.

4. The fastener as set forth in claim 2 wherein:
    (a) said abutment surface is a concavely radiused surface of revolution.

5. The fastener as set forth in claim 2 wherein:
    (a) said fastener is adapted to be used with a rod having a rod radius; and
    (b) said abutment surface is a concavely radiused surface of revolution having a concave radius substantially equal to the rod radius.

6. The fastener as set forth in claim 1 in combination with the rod and rod receiving member wherein:
    (a) when fully assembled, said rod receiving member includes a receiver surface positioned in at least partially surrounding relation to said rod; and
    (b) engagement of said second shaft segment with said rod surface urges said rod into frictional engagement with said receiver surface to further inhibit said rod from said rotation about said rod axis and from translation along the rod axis.

7. An apparatus including a rod receiving member and a set screw for securing an elongate rod within the rod receiving member so as to inhibit rotation of the rod about a rod axis and translation of the rod along the rod axis, the rod having a rod surface and said receiving member having a threaded bore with a bore radius, said set screw comprising:
    (a) a first screw shaft segment having a first radius with respect to a screw axis, said first radius being substantially equal to said bore radius, and said first screw shaft segment being compatibility threaded with respect to said threaded bore; said bore operably threadedly receiving said first screw shaft segment during use;
    (b) a second screw shaft segment extending coaxially from said first screw shaft segment and having a second radius; and
    (c) when said first screw shaft segment is fully within said bore, said threaded bore is so positioned and said second screw shaft is so sized and shaped as to have a radius that causes an outer threaded surface of said second screw shaft segment to interferingly engage said rod surface to thereby inhibit the rod from rotation about the rod axis and translation along the rod axis.

8. The apparatus as set forth in claim 7 and including:
    (a) an abutment surface connecting said first screw shaft segment and said second screw shaft segment and being sized and positioned to at least partially engage said rod surface to thereby urge the rod into frictional engagement with said receiving member.

9. The apparatus as set forth in claim 8 wherein:
    (a) said abutment surface is a concave surface of revolution.

10. The apparatus as set forth in claim 8 wherein:
    (a) said abutment surface is a concavely radiused surface of revolution.

11. The apparatus as set forth in claim 8 including the rod wherein:
    (a) said rod has a rod radius; and
    (b) said abutment surface is a concavely radiused surface of revolution having a concave radius substantially equal to said rod radius.

12. The apparatus as set forth in claim 7 including the rod wherein:
    (a) said rod receiving member includes a receiver surface sized, shaped and positioned to at least partially surround said rod when said rod is received therein; and (b) engagement of said second screw shaft segment with said rod surface during usage urges said rod into frictional engagement with said receiver surface to further inhibit said rod from rotating about said rod axis and from translating along said rod axis.

13. An apparatus including a rod receiving member and a set screw for securing within said rod receiving member an elongated rod so as to inhibit rotation of the rod about a rod axis and translation of the rod along the rod axis and wherein the rod has a rod surface and said receiving member has a threaded bore with a bore radius, said set screw comprising:

(a) a screw shaft having a first segment and a second segment; said screw shaft first segment having a first radius with respect to a screw axis, said first radius being substantially equal to said bore radius, and said first screw shaft segment being compatibly threaded with respect to said threaded bore; said bore operably threadedly receiving said first screw shaft segment;

(b) said second screw shaft segment extending coaxially from said first screw shaft segment and having an outer threaded surface with a second radius;

(c) an abutment surface coaxially connecting said first screw shaft segment and said second screw shaft segment; and (d) said threaded bore and said abutment surface being so sized and positioned respectively and said second screw shaft segment radius being sized so that said second segment threaded outer surface interferingly engages said rod surface, when said apparatus is in use, to thereby inhibit the rod from rotating about the rod axis and translating along the rod axis.

14. The apparatus as set forth in claim 13 and including:

(a) said abutment surface being sized and positioned to be adopted to at least partially engage the rod surface when the screw is inserted in the bore to thereby urge the rod into frictional engagement with said receiving member.

15. The apparatus as set forth in claim 13 wherein:

(a) said abutment surface is a concave surface of revolution.

16. The apparatus as set forth in claim 15 wherein:

(a) said abutment surface is a concavely radiused surface of revolution.

17. The apparatus as set forth in claim 15 including the rod wherein:

(a) said rod has a rod radius; and (b) said abutment surface is a concavely radiused surface of revolution having a concave radius substantially equal to said rod radius.

18. The apparatus as set forth in claim 13 including the rod wherein:

(a) said rod receiving member includes a receiver surface positioned in at least partially surrounding relation to said rod when in operative use; and (b) engagement of said second screw shaft segment threaded surface with said rod surface urges said rod into frictional engagement with said receiver surface to further inhibit said rod from rotating about said rod axis and from translating along said rod axis.

19. An apparatus including a rod receiving member and a set screw for securing an elongate rod from rotating about a rod axis and translating along said rod axis within said rod receiving member; said receiving member having a receiver surface sized and shaped to receive the rod in at least partially surrounding relation to the rod; said receiving member having a threaded bore with a bore thread and a bore radius; and said set screw comprising:

(a) a screw shaft having first and second segments; said first segment having a first radius with respect to a screw axis, said first radius being substantially equal to said bore radius, and said first segment having a first surface with a first thread thereon that is compatible with said bore thread so that said first screw shaft is threadedly receivable in said bore;

(b) said second segment extending coaxially from said first segment; said second segment having a second segment surface with a second radius and an external second thread thereon; said first radius being substantially greater than said second radius;

(c) an abutment surface connecting said first segment surface and said second segment surface, said abutment surface being a concavely radiused surface of revolution having a concave radius adapted to be substantially equal to the rod radius; and (d) said threaded bore and said abutment surface being so positioned respectively and said second segment radius being sized such that in use said abutment surface at least partially engages the rod surface to thereby urge said rod into frictional engagement with said receiver surface and with said second thread of said second screw shaft interferingly engages the rod surface to thereby inhibit the rod from rotating about said rod axis and translating along said rod axis.

20. The apparatus as set forth in claim 7 wherein:

(a) said second segment is sized so that engagement of said second segment with rod surface urges the rod into frictional engagement with said receiver surface to further inhibit the rod from rotating about the rod axis and from translating along the rod axis.

21. The apparatus as set forth in claim 19 and including:

(a) a break-off installation head connected to said first screw shaft segment in such a manner as to separate from said first screw shaft segment in response to relative torque therebetween exceeding a preselected level of torque.

22. The apparatus as set forth in claim 19 including said rod and wherein:

(a) said rod, said rod receiving member, and said set screw are adapted for implanting within a human body.

23. In a screw in fastener for securing an elongate rod within a rod receiving member, wherein such a rod has a rod surface, the improvement comprising:

(a) said fastener including a rotatable first shaft segment having a fastener axis and a first surface with a first radius; said first shaft segment having a threaded surface thereon; said first surface being sized and positioned such that when said set screw is fully inserted in said rod receiver during use, said threaded surface operably frictionally and tangentially engages said rod and urges the rod against the rod receiver; and (b) said fastener including a second shaft segment having a second radius and extending coaxially from said first shaft segment; said second shaft segment having a greater radius than said first shaft segment and adapted to be threadedly received in said receiving member.

24. The fastener as set forth in claim 23 and including:

(a) an abutment surface connecting said first shaft segment and said second shaft segment and positioned to be adapted to at least partially engage said rod surface when inserted in the rod receiver.

25. The fastener as set forth in claim 24 wherein:
(a) said abutment surface is a concavely radiused surface of revolution.

26. The fastener as set forth in claim 23 and including:
(a) a break-off head extending axially from said first shaft segment and being connected thereto in such a manner as to separate from said first shaft segment in response to relative torque therebetween exceeding a preselected level of torque.

27. In a medical implant apparatus including a set screw fastener, a rod receiver and a rod wherein said fastener secures the rod within the rod receiving member, and wherein the rod has a rod axis and a rod surface and the receiving member has a bore with a bore surface; said bore being aligned so that a central axis of bore does not align with said rod axis, the improvement comprising:

(a) said fastener being rotatably and threadedly received in said rod receiver bore along an axis of rotation; said fastener having a shaft segment with an externally threaded surface that is coaxial with the axis of rotation and that during use is sized and positioned relative to said rod receiving member such that said shaft segment threaded surface generally tangentially interferingly engages said rod surface when said set screw is fully received in said bore to thereby inhibit said rod from rotating about said rod axis within said rod receiving member; and (b) said fastener including an abutment surface extending outward from said shaft segment and being sized and positioned so that, when in use with said rod, said abutment surface at least partially engages said rod surface to thereby urge said rod into frictional engagement with said receiving member.

28. The apparatus as set forth in claim 27 wherein said shaft segment is a rod engaging shaft segment and including:
(a) a mounting shaft segment extending coaxial with said rod engaging shaft segment; and
(b) said mounting shaft segment is operably threaded into a bore in with said rod receiving member.

29. The apparatus as set forth in claim 28 wherein:
(a) said mounting shaft segment has a greater diameter than said rod engaging shaft segment.

30. The apparatus as set forth in claim 29 wherein:
(a) said abutment surface is located at a transition from said mounting shaft segment to said rod engaging shaft segment.

31. The apparatus as set forth in claim 27 wherein:
(a) said abutment surface is a concavely radiused surface of revolution.

* * * * *

UNITED STATES PATENT AND TRADEMARK OFFICE
CERTIFICATE OF CORRECTION

PATENT NO. : 6,699,248 B2
DATED : March 2, 2004
INVENTOR(S) : Roger P. Jackson

It is certified that error appears in the above-identified patent and that said Letters Patent is hereby corrected as shown below:

Column 7,
Lines 32-57, should read as follows:
1. A fastener sized and shaped so as to be adapted to secure an elongate rod within a rod receiving member wherein the rod has a rod axis and a rod surface and the receiving member has a threaded bore; said fastener comprising:
   (a) a first shaft segment having a fastener axis and a first radius with a threaded outer surface adapted to be threaded into said threaded bore about an axis of rotation;
   (b) a second shaft segment having a second radius of a smaller size than said first radius and extending coaxially from said first shaft segment;
   (c) said first shaft segment being rigid and shaped to be rotatably received within the bore so as to retain said first shaft segment therein with said second shaft segment extending outwardly from the bore; and
   (d) said fastener being sized and shaped so that when said shaft first segment is fully received in said bore, said second shaft segment second radius is sized such that said second shaft segment interferingly engages said rod surface along a substantial segment thereof to thereby inhibit rotation of said rod about said rod axis and translation of said rod along said rod axis relative to the receiving member.

Column 10,
Lines 29-35, should read as follows:
20. The apparatus as set forth in claim 19 wherein:
   (a) said second segment is sized so that engagement of said second segment with rod surface urges the rod into frictional engagement with said receiver surface to further inhibit the rod from rotating about the rod axis and from translating along the rod axis.

Signed and Sealed this

Twenty-second Day of March, 2005

JON W. DUDAS
*Director of the United States Patent and Trademark Office*